United States Patent
Buan Murphy et al.

(10) Patent No.: US 10,533,192 B2
(45) Date of Patent: Jan. 14, 2020

(54) PRODUCTION OF ISOPRENE BY METHANE-PRODUCING ARCHAEA

(71) Applicant: NUtech Ventures, Lincoln, NE (US)

(72) Inventors: Nicole Roswitha Buan Murphy, Lincoln, NE (US); Karrie A. Weber, Lincoln, NE (US); Jared Thomas Aldridge, Lincoln, NE (US); Sean Robert Carr, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 16 days.

(21) Appl. No.: 15/383,332

(22) Filed: Dec. 19, 2016

(65) Prior Publication Data

US 2017/0175145 A1    Jun. 22, 2017

Related U.S. Application Data

(60) Provisional application No. 62/271,151, filed on Dec. 22, 2015.

(51) Int. Cl.
| | | |
|---|---|---|
| *C12N 1/21* | (2006.01) | |
| *C12N 9/88* | (2006.01) | |
| *C12N 15/60* | (2006.01) | |
| *C12P 5/02* | (2006.01) | |

(52) U.S. Cl.
CPC .......... *C12P 5/023* (2013.01); *C12N 9/88* (2013.01); *C12Y 402/03027* (2013.01)

(58) Field of Classification Search
None
See application file for complete search history.

(56) References Cited

U.S. PATENT DOCUMENTS

| 5,342,769 A | 8/1994 | Hunter et al. |
| 7,732,680 B2 | 6/2010 | Kourtz et al. |
| 8,326,547 B2 | 12/2012 | Liu et al. |
| 2014/0113344 A1 | 4/2014 | Hayashi et al. |
| 2014/0234926 A1 | 8/2014 | Beck et al. |

FOREIGN PATENT DOCUMENTS

| EP | 2334788 A1 | 6/2011 | |
| WO | 1998049106 A1 | 11/1998 | |
| WO | 2009038530 A1 | 3/2009 | |
| WO | 2010078457 A2 | 7/2010 | |
| WO | 2013181647 A2 | 12/2013 | |
| WO | 2014138419 A1 | 9/2014 | |
| WO | WO-2014193473 A1 * | 12/2014 | ............ C12P 19/32 |

OTHER PUBLICATIONS

Reeve, Molecular biology of methanogens, Annu. Rev. Microbiol., 1992, 46, 165-91.*
Welander et al., Mutageneis of the C1 oxidation pathway in Methanosarcina barkeri, J. Bacteriol., 2008, 190, 1928-36.*
Puigbo et al., Optimizer: a web server for optimizing the codon usage of DNA sequences, Nucleic Acid Res., 2007, 35, W126-31.*
GenBank, Accession No. AB198180, 2005, www.ncbi.nlm.nih.gov.*
Nakamura et al., "Codon usage tabulated from international DNA seqeunce databases," Nuc. Acids Res., 2000, 28, 292.*
J. De Vrieze, et al., The rediscovered methanogen for heavy duty biomethanation, Bioresource Technology 112 (2012) pp. 1-9, 2012.
S. Guiot, et al., Potential of Wastewater-Treating Anaerobic Granules for Biomethanation of Synthesis Gas, Environmental Science & Technology, 2006, pp. 1-7.
A. N. Hassan, et al., Invited review: Anaerobic fermentation of dairy food wastewater, J. Dairy Sci., 95: pp. 6188-6203, 2012.
H. Sahm, Anaerobic Wastewater Treatment, fur Biotechnologie der Kernforschungsanlage julich, D-5170 Julich, FRG, pp. 1-33.
BLAST Help Manual, pp. 1-13. 2016.
V. Soo, et al., Reversing methanogenesis to capture methane for liquid biofuel precursors, Microb Cell Fact (2016), 15:11, pp. 1-14.
K. Sowers, et al., Disagregation of Methanosarcina spp. and Growth as Single Cells at Elevated Osmolarity, Applied and Environmental Microbiology, Nov. 1993, pp. 3832-3839.
M. Li, et al., Harnessing homologous recombination in vitro to generate recombinant DNA via SLIC, Nature Methods, vol. 4, No. 3, Mar. 2007, pp. 251-256.
W. Pearson, [5] Rapid and Sensitive Sequence Comparison with FASTP and FASTA, Methods in Enzymology, vol. 183, pp. 63-98.

* cited by examiner

*Primary Examiner* — Robert B Mondesi
*Assistant Examiner* — Todd M Epstein
(74) *Attorney, Agent, or Firm* — Stinson LLP

(57) ABSTRACT

Plasmid vectors and use of plasmid vectors in methods for producing methane and isoprene using *Archaea* are disclosed. Particularly, plasmid vectors that express isoprene synthase (ispS) are prepared and inserted into methanogens, such as *Methanosarcina acetivorans*, to allow for co-production of methane and isoprene. In one embodiment, the methods of the present disclosure can be used for wastewater management.

9 Claims, 9 Drawing Sheets
(1 of 9 Drawing Sheet(s) Filed in Color)
Specification includes a Sequence Listing.

SEQUENCE LISTING

<160> NUMBER OF SEQ ID NOS: 5

<210> SEQ ID NO 1
<211> LENGTH: 1797
<212> TYPE: DNA
<213> ORGANISM: Artificial Sequence
<220> FEATURE:
<223> OTHER INFORMATION: Synthetic

<400> SEQUENCE: 1

```
catatgatgg ctaccgaact tctttgtctg catagaccta tctcccttac ccataaactg      60
ttcagaaatc ctcttcctaa agttattcag gcaacccctc ttacccttaa actgagatgc     120
tccgtttcca ccgaaaatgt atcctttacc gaaaccgaaa ccgaagcaag aagatccgca     180
aattatgaac ctaattcctg ggattatgat tatcttcttt cctccgatac cgatgaatcc     240
attgaagttt ataagataa agctaagaaa cttgaagcag aagttagaag agaaattaat      300
aatgaaaagg cagaatttct taccttctt gaacttattg ataatgttca gagacttgga     360
cttggatata gatttgaatc cgatattaga ggagcacttg atagatttgt ttcctccgga     420
ggattcgatg cagttaccaa aacatccctt catggaaccg cactttcctt tagactgctt     480
agacagcatg gatttgaagt tagccaggaa gcatttccg gatttaaaga tcagaatgga     540
aattttcttg aaaatcttaa agaagatatt aaagcaattc tttcccttta tgaagcatcc     600
tttcttgcac ttgaaggaga aaatattctt gatgaagcaa aagtatttgc aatttcccat     660
cttaaagaac tttccgaaga aaagattgga aaagaacttg cagaacaggt taatcatgca     720
cttgaacttc ctcttcatag aagaacccag agacttgaag cagtttggtc cattgaagca     780
tataggaaga aagaagatgc aaatcaggtt cttcttgaac ttgcaattct tgattataat     840
atgattcagt ccgtttatca gagagatctt agagaaacct ccagatggtg gagaagagtt     900
ggacttgcaa ccaaacttca ttttgcaaga gatagactta ttgaatcctt ttattgggca     960
gttggagttg catttgaacc tcagtattcc gattgcagaa attccgttgc taaaatgttt    1020
tcctttgtta ccattattga tgatatttat gatgtttatg gaacccttga tgaacttgaa    1080
cttttcaccg atgcagttga aagatgggat gttaatgcaa ttaatgatct tcctgattat    1140
atgaaacttt gctttcttgc actttataat accattaatg aaattgcata tgataatctt    1200
aaagacaaag gagaaaatat tcttccttat cttaccaaag catgggcaga tctttgcaat    1260
```

-continued

| | |
|---|---|
| gcatttcttc aggaagcaaa atggctttat aataaatcca cccctacctt tgatgattat | 1320 |
| tttggaaatg catggaaatc ctcctccgga cctcttcagc ttgtatttgc atattttgca | 1380 |
| gttgttcaga atattaagaa agaagaaatt gaaaatcttc agaaatatca tgataccatt | 1440 |
| tccagacctt cccatatctt tagactttgc aatgatcttg catccgcatc cgcagaaatt | 1500 |
| gcaagaggag aaaccgcaaa ttccgtttcc tgctatatga gaaccaaagg aatttccgaa | 1560 |
| gaacttgcaa ccgaatccgt tatgaatctt attgatgaaa cctggaagaa atgaataaa | 1620 |
| gagaaacttg gaggatccct tttcgcaaaa ccttttgttg aaaccgcaat taatcttgca | 1680 |
| agacagagcc attgcaccta tcataatgga gatgcacata cctcccctga tgaacttacc | 1740 |
| aggaaaagag ttctttccgt tattaccgaa cctattcttc cttttgaaag aggatcc | 1797 |

<210> SEQ ID NO 2
<211> LENGTH: 1686
<212> TYPE: DNA
<213> ORGANISM: Artificial Sequence
<220> FEATURE:
<223> OTHER INFORMATION: Synthetic

<400> SEQUENCE: 2

| | |
|---|---|
| catatgtccg tttccaccga aaatgtatcc tttaccgaaa ccgaaaccga agcaagaaga | 60 |
| tccgcaaatt atgaacctaa ttcctgggat tatgattatc ttcttttcctc cgataccgat | 120 |
| gaatccattg aagtttataa agataaagct aagaaacttg aagcagaagt tagaagagaa | 180 |
| attaataatg aaaaggcaga atttcttacc cttcttgaac ttattgataa tgttcagaga | 240 |
| cttggacttg gatatagatt tgaatccgat attagaggag cacttgatag atttgtttcc | 300 |
| tccggaggat tcgatgcagt taccaaaaca tcccttcatg gaaccgcact ttcctttaga | 360 |
| ctgcttagac agcatggatt tgaagttagc caggaagcat tttccggatt taaagatcag | 420 |
| aatggaaatt tccttgaaaa tcttaaagaa gatattaaag caattctttc cctttatgaa | 480 |
| gcatccttc ttgcacttga aggagaaaat attcttgatg aagcaaaagt attgcaatt | 540 |
| tcccatctta aagaactttc cgaagaaaag attggaaaag aacttgcaga acaggttaat | 600 |
| catgcacttg aacttcctct tcatagaaga acccagagac ttgaagcagt ttggtccatt | 660 |
| gaagcatata ggaagaaaga agatgcaaat caggttcttc ttgaacttgc aattcttgat | 720 |
| tataatatga ttcagtccgt ttatcagaga gatcttagag aaacctccag atggtggaga | 780 |
| agagttggac ttgcaaccaa acttcatttt gcaagagata gacttattga atcctttat | 840 |
| tgggcagttg gagttgcatt tgaacctcag tattccgatt gcagaaattc cgttgctaaa | 900 |
| atgtttttcct tgttaccat tattgatgat atttatgatg tttatggaac ccttgatgaa | 960 |
| cttgaacttt tcaccgatgc agttgaaaga tgggatgtta atgcaattaa tgatcttcct | 1020 |
| gattatatga actttgctt tcttgcactt tataatacca ttaatgaaat tgcatatgat | 1080 |
| aatcttaaag acaaaggaga aaatattctt ccttatctta ccaaagcatg ggcagatctt | 1140 |
| tgcaatgcat ttcttcagga agcaaaatgg ctttataata aatccacccc tacctttgat | 1200 |
| gattattttg gaaatgcatg gaaatcctcc tccggacctc ttcagcttgt atttgcatat | 1260 |
| tttgcagttg ttcagaatat taagaaagaa gaaattgaaa tcttcagaa atatcatgat | 1320 |
| accatttcca gaccttccca tatctttaga ctttgcaatg atcttgcatc cgcatccgca | 1380 |
| gaaattgcaa gaggagaaac cgcaaattcc gtttcctgct atatgagaac caaaggaatt | 1440 |
| tccgaagaac ttgcaaccga atccgttatg aatcttattg atgaaacctg gaagaaaatg | 1500 |

```
aataaagaga aacttggagg atccctttc gcaaaaccttt tgttgaaac cgcaattaat    1560 cttgcaagac agagccattg cacctatcat aatggagatg cacataccctc ccctgatgaa  1620 cttaccagga aaagagttct ttccgttatt accgaaccta ttcttccttt tgaaagatga   1680
ggatcc                                                             1686

<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3
attaaggagg aaattcatat ggctaccgaa cttctttgtc t                      41

<210> SEQ ID NO 4
<211> LENGTH: 41
<212> TYPE: DNA
<213> ORGANISM: Artificial Sequence
<220> FEATURE:
<223> OTHER INFORMATION: Synthetic

<400> SEQUENCE: 4
attaaggagg aaattcatat gtccgtttcc accgaaaatg t                      41

<210> SEQ ID NO 5
<211> LENGTH: 44
<212> TYPE: DNA
<213> ORGANISM: Artificial Sequence
<220> FEATURE:
<223> OTHER INFORMATION: Synthetic

<400> SEQUENCE: 5
cgagggccca agcttggatc ctcatctttc aaaaggaaga atag                   44
```

PRODUCTION OF ISOPRENE BY METHANE-PRODUCING ARCHAEA

CROSS REFERENCE TO RELATED APPLICATIONS

This application claims priority to U.S. Provisional Patent Application No. 62/271,151 filed on Dec. 22, 2015, the disclosure of which is hereby expressly incorporated by reference in its entirety.

INCORPORATION OF SEQUENCE LISTING

A paper copy of the Sequence Listing and a computer readable form of the sequence containing the file named "NUtech_2016-014_ST25", which is 5,702 bytes in size (as measured in MICROSOFT WINDOWS® EXPLORER), are provided herein and are herein incorporated by reference. This Sequence Listing consists of SEQ ID NOs: 1-5.

BACKGROUND OF THE DISCLOSURE

The present disclosure relates generally to methods for converting inorganic carbon as a solid mineral (such as, but not limited to, carbonates), aqueous species (such as, but not limited to, bicarbonate) or gas (such as, but not limited to, carbon dioxide ($CO_2$))—from energy generation facilities into a biofuel and a bioproduct. More particularly, the present disclosure relates to methods for producing methane and isoprene using *Archaea*. In one particularly suitable embodiment, the methods of the present disclosure can be used for wastewater management.

Carbon capture and utilization strategies (CCUS) are critical to minimize emissions or remove anthropogenic $CO_2$ from the atmosphere. Yet, green technologies converting $CO_2$ to value-added products in addition to biofuels is lagging.

To date, 30-40% of emitted $CO_2$ results from coal fired power plants and technologies have been developed to remove $CO_2$ from emissions. Additionally, wastewater treatment, such as in municipal, agricultural and industrial waste treatment has gained popularity. Particularly, the demand for water and wastewater treatment products in the top 40 national markets was 47.7 billion in 2012. This total market is expected to reach nearly $53.1 billion in 2013, $59.2 billion in 2014 and about $96.3 billion by 2019, with a compound annual growth rate of 10.2% for the period of 2014 to 2019.

One of the technologies for $CO_2$ removal is the production of carbonate minerals such as calcium carbonate. Further, early microbial wastewater treatment typically involves the breaking down of complex organic matter by microbes, which results in the formation of acetate, formate, methanol, methylamines, $H_2$ and $CO_2$. These compounds accumulate to inhibitory levels in the anaerobic digester if not converted into $CH_4$. Methane-producing microbial species in pure culture and in multi-organism microbial consortia are naturally capable of using anthropogenic carbonates or $CO_2$ for production of isoprene, which they incorporate into branched alkane lipids that constitute cell membranes. *Methanosarcinales* methanogens are the most metabolically diverse methanogens and can grow efficiently on most methanogenic substrates and/or methane gas ($CH_4$).

It would be advantageous if engineered methanogens could be introduced to the anaerobic digesters to augment the existing population of "wild" methanogens. Additionally, metagenomics analysis of the microbial community already present in the desired wastewater treatment would allow for selection, cultivation, and engineering of dominant strains, which feed on wastewater products to maximize methane and isoprene production.

BRIEF DESCRIPTION OF THE DISCLOSURE

The present disclosure is generally related to methods of engineering microbial strains capable of producing isoprene and methane. The engineered strains could then be used in methods of $CO_2$ removal in the atmosphere, and in some embodiments, used in wastewater management. Particularly, the present disclosure has created plasmids that express isoprene synthase (ispS). For example, when the plasmids are inserted into methanogens, such as *Methanosarcina acetivorans*, the microbial strains are capable of producing methane and isoprene. In one particularly suitable embodiment, the plasmids are created for use in methods of wastewater management.

Particularly, in one aspect, the present disclosure is directed to a host cell comprising a vector comprising a nucleic acid encoding isoprene synthase.

In another aspect, the present disclosure is directed to a vector comprising a nucleic acid encoding isoprene synthase.

In yet another aspect, the present disclosure is directed to a method of preparing a microbial strain capable of co-producing methane and isoprene. The method comprises: preparing a vector comprising a nucleic acid encoding isoprene synthase; introducing the vector into a host cell; and culturing the host cell including the vector.

In another aspect, the present disclosure is directed to a method of preparing a microbial strain capable of producing isoprene from methane gas or biogas. The method comprises: preparing a vector comprising a nucleic acid encoding isoprene synthase; introducing the vector into a host cell; and culturing the host cell including the vector.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein.

DETAILED DESCRIPTION

Figure 1A:
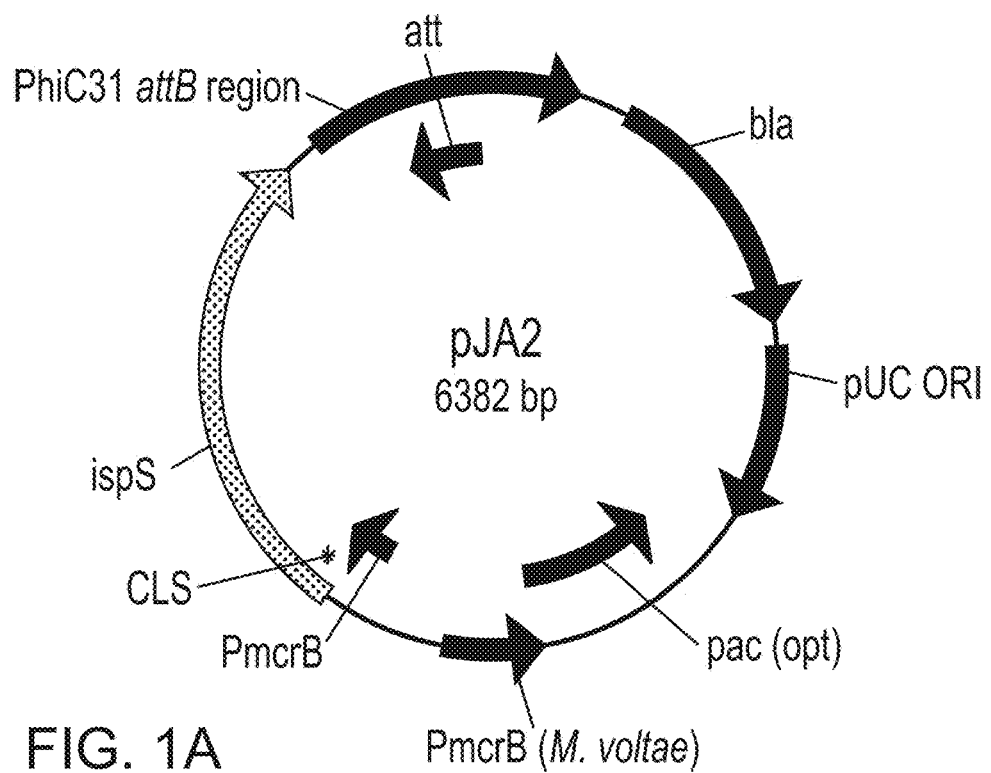
FIG. 1A depicts a plasmid vector map of one exemplary plasmid vector for use in the methods of the present disclosure.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is generally directed to methods for producing methane and isoprene using *Archaea*. More particularly, the present disclosure is directed to the use of methanogens, and in particularly suitable embodiments, *Methanosarcina acetivorans* or *Methanosarcina barkeri*, transfected with engineered plasmid vectors that allow for the methanogens to co-produce isoprene and methane. The plasmid vectors can be stably integrated into the methanogen chromosome to reduce the probability that the isoprene-production trait could be lost.

Generally, the present disclosure provides plasmid vectors including a nucleic acid encoding an isoprene synthase (ispS). Isoprene synthase (ispS) is an enzyme that converts dimethylallyl diphosphate into isoprene. In one aspect, the codons of the ispS protein sequence can be "semi-optimized" such that most codons are adjusted to match the *Methanosarcina* tRNA abundances. In several positions low-frequency tRNA can be selected to decrease gene expression so that isoprene production is not lethal. Suitable primers for use in providing the plasmid vectors include the primers with nucleotide sequences represented by SEQ ID NO:3, SEQ ID NO: 4 and SEQ ID NO:5.

Further, in one embodiment, the plasmid vectors of the present disclosure include the nucleic acid having (i) the nucleotide sequence represented by SEQ ID NO:1, or (ii) the nucleotide sequence represented by SEQ ID NO:2, which is the nucleotide sequence consisting of the nucleotide residues at positions 1-3701 and 3813-6382 in the nucleotide sequence represented by SEQ ID NO:1. The nucleotide sequence consisting of the nucleotide residues at positions 3702-3812 can encode a putative chloroplast localization signal (CLS).

In another embodiment, the nucleic acid includes a nucleotide sequence having 90% or more identity to the nucleotide sequence of (i) or (ii) above, and encodes a protein having an isoprene synthase activity. The percent identity to the nucleotide sequence may be 91%, 92%, 93%, 94%, 95%, 96%, 97%, 98%, or 99% or more. The isoprene synthase activity, as used herein, refers to an activity to form isoprene from dimethylallyl diphosphate (DMAPP) or isopentenyl pyrophosphate.

The percent identity of the nucleotide sequences can be determined using algorithm BLAST (Pro. Natl. Acad. Sci. USA, 90, 5873 (1993)) by Karlin and Altschul, and FASTA (Methods Enzymol., 183, 63 (1990)) by Pearson. The programs referred to as BLASTP and BLASTN were developed based on this algorithm BLAST (see, www.ncbi.nlm nih-.gov). Thus, the percent identity of the nucleotide sequences may be calculated using these programs with default setting. The lowest value among the values derived from these calculations may be employed as the percent identity of the nucleotide sequences.

Figure 1B:
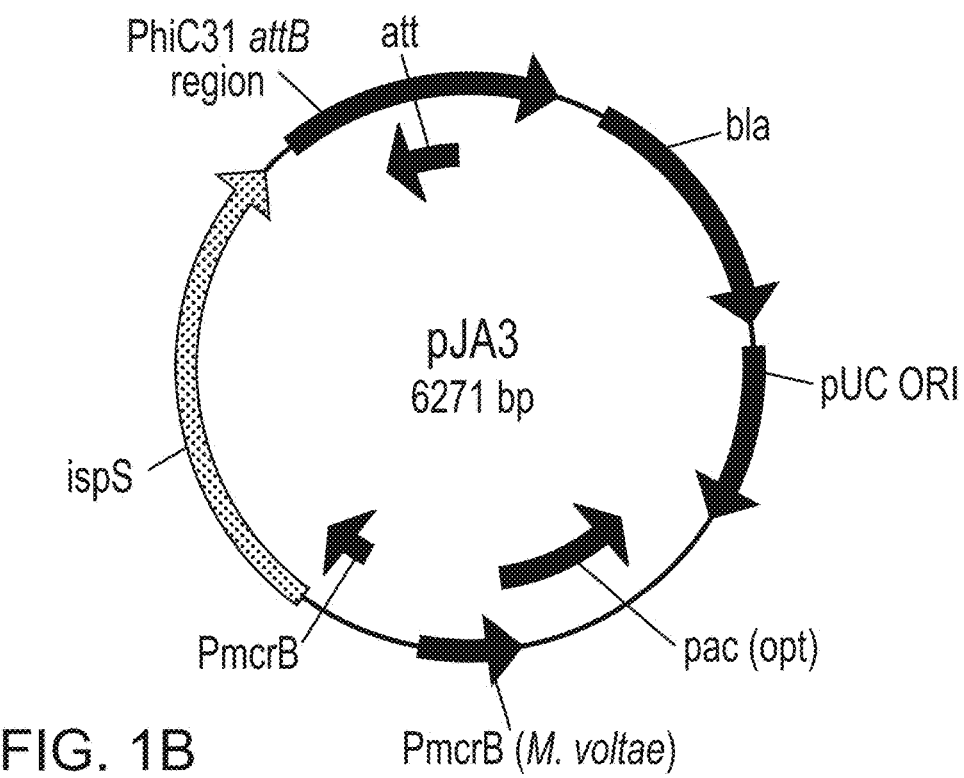
FIG. 1B depicts a plasmid vector map of another exemplary plasmid vector for use in the methods of the present disclosure.

Exemplary plasmid vectors prepared using the methods of the present disclosure are shown in FIGS. 1A & 1B. As shown, the plasmid vectors of FIGS. 1A & 1B include the strong constitutive promoter PmcrB. The difference in the two plasmid vectors is that the plasmid vector shown in FIG. 1A includes CLS, while the plasmid vector shown in FIG. 1B does not include CLS. Additionally suitable plasmid vectors include vectors similar to those shown in FIGS. 1A & 1B with the exception of using a tetracycline-inducible promoter, Ptet.

The present disclosure further provides a transformant comprising the plasmid vector. The transformant of the present disclosure is one obtained by introducing the plasmid vector of the present disclosure into a host chromosome. The host used for the present invention is preferably a microorganism such as an *Archaea*, a bacterium (both gram-positive or gram-negative) or a fungus. In particularly suitable embodiments, the host includes methanogens. Methanogens are grown in HS+MeOH media until $OD_{600}$ reaches about 0.5 to 0.7 and then transfected with the plasmids using conventional methods. While described herein as using *M. acetivorans* and *M. barkeri*, it should be understood that any *Methanosarcina* strains can be used as the host cells without departing from the scope of the present disclosure. Further, it is believed that the plasmids and vector system should be capable of ispS functionality in any methanogen, methanotroph, or acetogen.

Advantageously, the methanogens can use any carbon source known in the art for making isoprene. In some embodiments, methanogens (e.g., *M. acetivorans* and *M. barkeri*) can use syngas (i.e., gaseous mixtures of any one or several of: CO, $CH_4$, $H_2+CO_2$), such as derived from cellulosic biomass by thermal cracking or coal production, as a growth substrate. Other suitable growth substrates include for example, methanol (and methoxy compounds), methylamines (monomethylamine, dimethylamine, trimethylamine, and derivatives), methylsulfides (methanethiol, dimethylsulfide and derivatives), methylated metal/metalloids, formate, carbonate, graphite, carbon monoxide, acetate, and the like, and combinations thereof.

Figure 3A:
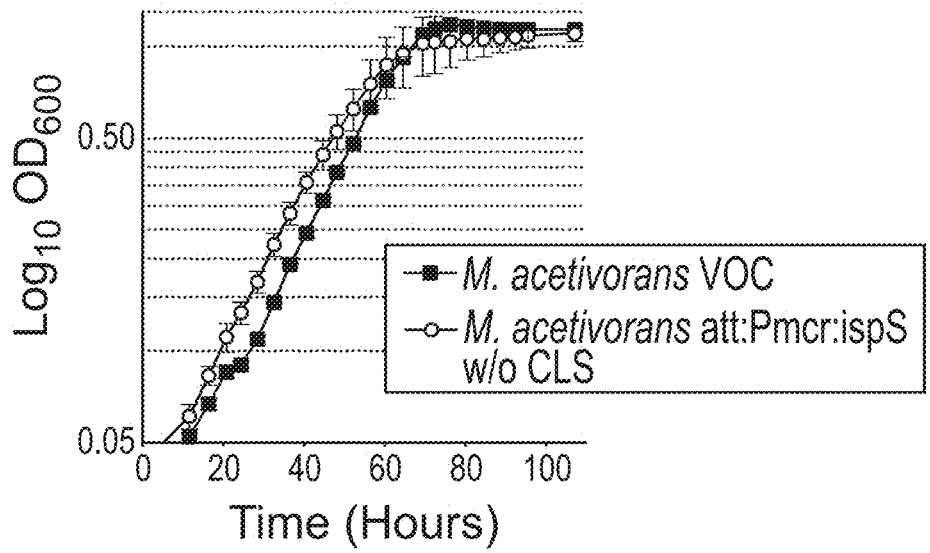
FIG. 3A depicts *M. acetivorans* growth on TMA as analyzed in Example 1.
Figure 3B:
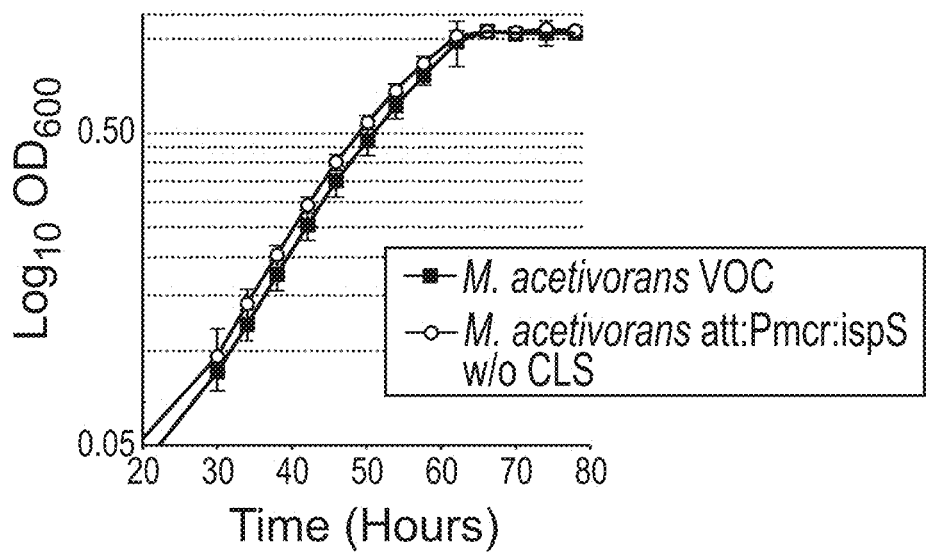
FIG. 3B depicts *M. acetivorans* growth on MeOH as analyzed in Example 1.

It was found that once transfected, the methanogen host cells co-produce methane and isoprene. It was expected that isoprene production would result in a decrease in methane as carbon should be directed towards isoprene. As shown in the Examples below, expression of ispS had a 30% decrease in methane production in *M. barkeri*, which indicates these adapted cells may be producing as much as 6% isoprene per mole basis. Further, a surprisingly large effect on methane production was seen in the ispS-producing *M. acetivorans* strains, which were "missing" 87% of the carbon, which would translate to a 17.6% isoprene production efficiency per mol basis (FIGS. 3A & 3B).

It is believed that the plasmid vectors engineered herein and used in the methods of the present disclosure would be advantageous in many industries, including municipal, agricultural, and industrial waste treatment, and in a particularly suitable aspect, the methods are used in wastewater treatment plants. Conventionally, isoprene can be produced by engineered *E. coli*, yeast or algae, but because they are different organisms, each has different requirements for feedstocks. Depending on the organism, each has different requirements for a production facility: algae must be aerated, while *E. coli* and yeast can be grown under aerated or anaerobic conditions using glucose or protein feedstocks. As such, methanogen technologies, such as the methods of the present disclosure, can be used in anaerobic digesters and anaerobic fermentation technologies using *E. coli* or yeasts to improve yield of upstream value-added bioproducts. The methanogens will increase efficiency and overall yield of microbial conversion technologies and improve the overall economic profit margins for those technologies (see FIGS. 9A-9D). The lack of specialized facilities to grow methanogens and collect bioproducts is a significant advantage versus algae technologies or aerobic microbial technologies, which require effort, energy, and cost to add oxygen.

Other industries that are drop-in compatible with the methods of the present disclosure include, by way of example only, ethanol, butanol and other transportation or renewable solvent or biodiesel production facilities, syngas bioproduct facilities, renewable bioplastics, vitamins and amino acids and the like produced by microbial fermentation (e.g., animal feed additives, human food additives, plastics, cosmeceuticals), and the like. One further industry includes the coal industry.

EXAMPLES

Example 1

In this Example, plasmid vectors were engineered and cells were transfected with the plasmid vectors. The ability of the cells to produce isoprene and methane was then analyzed.

Initially, cDNA of the isoprene synthase from *Populus alba* was obtained by RT-PCR with the total RNA obtained as a template using primers designed based on the analyzed nucleotide sequence information of the isoprene synthase gene from *Populus alba*. Particularly, plasmids were engineered using the protocol adapted from Li et al., "Harnessing homologous recombination in vitro to generate recombinant DNA via SLIC," Nat Meth 4, 251-256 (2007), in which the primers are designed with a 25-basepair homology with the parental plasmid (i.e., pNB730) following digestion (insertion into multiple cloning site (MCS)) as well as a 15-20 basepair homology to isoprene synthase (ispS) from *P. alba*. Particularly, 2 μg of parental plasmid was digested with restriction enzymes. The primers have the nucleotide sequences of SEQ ID NO:3, SEQ ID NO:4, or SEQ ID NO:5.

After digestion, linearized parental plasmid was purified following PCR Clean up protocol (commercially available as WIZARD® SV Gel and PCR Clean-Up System (Promega, Madison, Wis.) Ample amount of restriction enzyme as well as enough time for complete digestion (e.g., at least 3 hours) was provided. DNA from the Clean up column was eluted with ddH$_2$O. ispS was PCR-amplified following the Phusion Flash protocol (commercially available as Phusion High-Fidelity DNA Polymerase, Thermo Scientific, Lenexa, Kans.) using the primers as designed above. The amplified gene of interest was purified using PCR Clean up protocol, and DNA was eluted from the Clean up column using ddH$_2$O.

T4 Treatment

Next, 1 μg of digested parental plasmid and 1 μg of the amplified ispS were separately treated with 0.5 U of T4 DNA polymerase in 1×NEBuffer 2 plus BSA in a 20 μl reaction at room temperature for 30 minutes. The reaction was stopped by adding ⅒ total volume of 10 mM dCTP and left on ice.

Annealing Mixture

After the T4 treatment was completed, a 10 μL annealing reaction was conducted using a 1:1 ispS to parental plasmid molar ratio. The amount of parental plasmid was 150 ng. 1× ligation buffer (NEB), appropriate amount of T4 treated ispS (1:1 molar ratio between parental T4 treated plasmid and T4 treated ispS), and water were then added to the parental plasmid. The mixture was incubated in a 37° C. water bath for 30 minutes. After the reaction, the mixture was returned to ice until further use.

Transformation

5 μL of the annealed mixture was added to 150 μL of chemically competent cells (*E. coli*), the mixture was incubated on ice for 30 minutes, heat shocked at 42° C. for 45 seconds, and then returned to ice for 2 minutes. 0.9 mL of super optimal broth with catabolite repression (SOC) was added to the mixture, the cells were allowed to recover at 37° C. for 1 hour. After recovery, cells were plated on LB agar plates supplemented with 100 mg/L ampicillin and incubated overnight at 37° C.

Transfecting cells with the plasmids.

All of the following methods were performed anaerobically in a 20% $CO_2$/5% $H_2$/75% $N_2$ environment unless otherwise stated. Methanogens were grown in HS+MeOH media, 10 ml culture per transformation for *M. acetivorans* and 40 ml culture per transformation for *M. barkeri*. Cells were grown at 35° C. for two days or until $OD_{600}$ reached between 0.5-0.7. Cells were concentrated via clinical centrifugation (15 minutes for *M. acetivorans*, 2 minutes for *M. barkeri*) and media removed. 2 μg of Vector DNA was diluted to 50 μl with sucrose and prepared with DOTAP reagent in sterile borosilicate glass test tubes according to the manufacturer's protocol. DNA and DOTAP was gently mixed and incubated at room temperature for 15 minutes. Cell pellets were resuspended in 1 mL of sucrose and added directly into the DNA/DOTAP solution. The solution was allowed to incubate for 4 hours at room temperature. The entire volume of the solution was then added to 25 mL of fresh high salt medium (HS)+MeOH (40 mM) media and incubated overnight (~16 hours) at 35° C. (Sowers et al., 1993 Appl Env Microbiol. P3832-3839).

*M. acetivorans* was plated on agar plates by applying the cells directly onto agar, whereas *M. barkeri* was first mixed with a 0.5% top agar then applied gently to the agar plate. Plates were incubated under $H_2S$ for 14 days and checked for colony formation. Isolated colonies were streaked for selection on agar plates containing puromycin.

Figure 2:
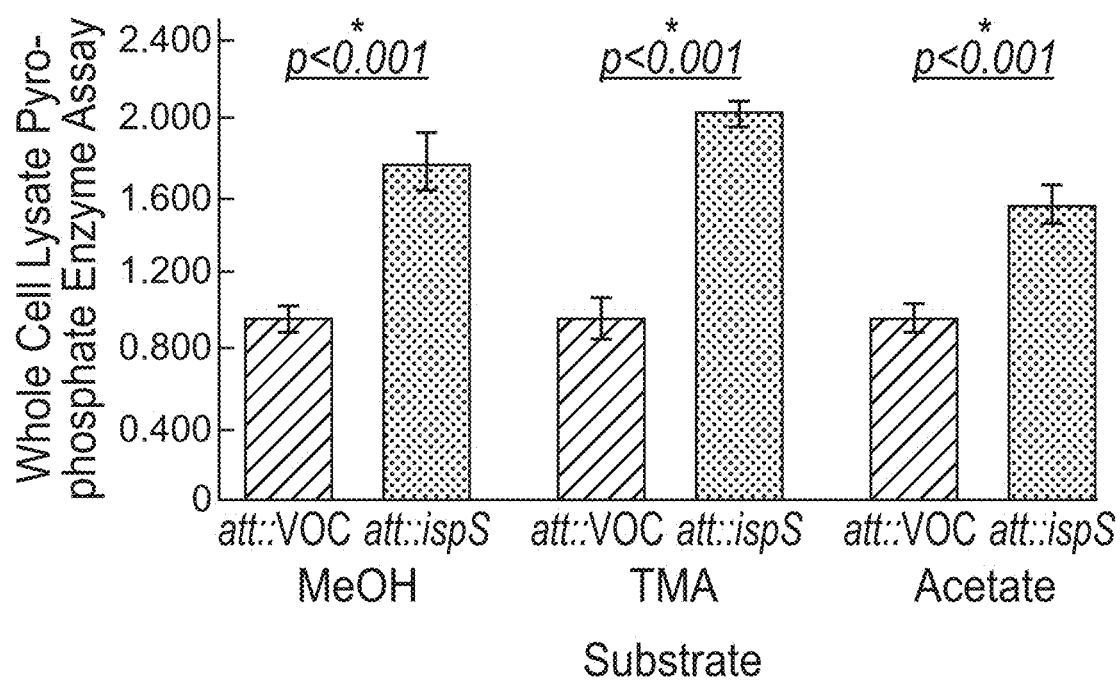
FIG. 2 depicts increased enzymatic activity in *M. acetivorans* cells, which have been transformed with the exemplary plasmid when grown on TMA, MeOH, or acetate as the carbon source.

A *M. acetivorans* vector only control (VOC) and an ispS expressing strain of *M. acetivorans* were grown anaerobically in 10 mL HS media containing either 125 mM methanol (MeOH), 40 mM trimethylamine (TMA), or 120 mM acetate. Cells were collected and the EnzCheck pyrophosphatase biochemical assay kit (ThermoFisher Scientific) was used to confirm the introduced ispS gene resulted in increased pyrophosphate production from isopentenyl-pyrophosphate in whole cell lysates. It should be understood that normal cells will produce pyrophosphate from isopentenyl-pyrophosphate as a part of normal cellular lipid synthesis. In this assay, higher pyrophosphate release from isopentenyl-pyrophosphate indicates either higher lipid synthesis or isoprene production from the isopentenyl-pyrophosphate substrate. As shown in FIG. 2, strains expressing ispS had higher enzymactic activity as compared to the vector only control (VOC) strains.

A M. acetivorans vector only control (VOC) and an ispS expressing strain of M. acetivorans were grown anaerobically in 10 mL HS media containing 40 mM trimethylamine (TMA). Optical density at 600$_{nm}$ was recorded using a Spectronic 20D+ (Thermo Scientific, Waltham, Mass.) at 4 hour increments. As shown in FIG. 3A, transfecting M. acetivorans cells with an ispS plasmid vector did not negatively affect the growth of M. acetivorans in TMA. Additionally, a M. acetivorans vector only control (VOC) and an ispS expressing strain of M. acetivorans were grown anaerobically in 10 mL HS media containing 125 mM methanol (MeOH). Optical density at 600$_{nm}$ recorded using the Spectronic 20D+ at 4 hour increments. As shown in FIG. 3B, transfecting M. acetivorans cells with an ispS plasmid vector did not negatively affect the growth of M. acetivoran in MeOH.

Figure 5:
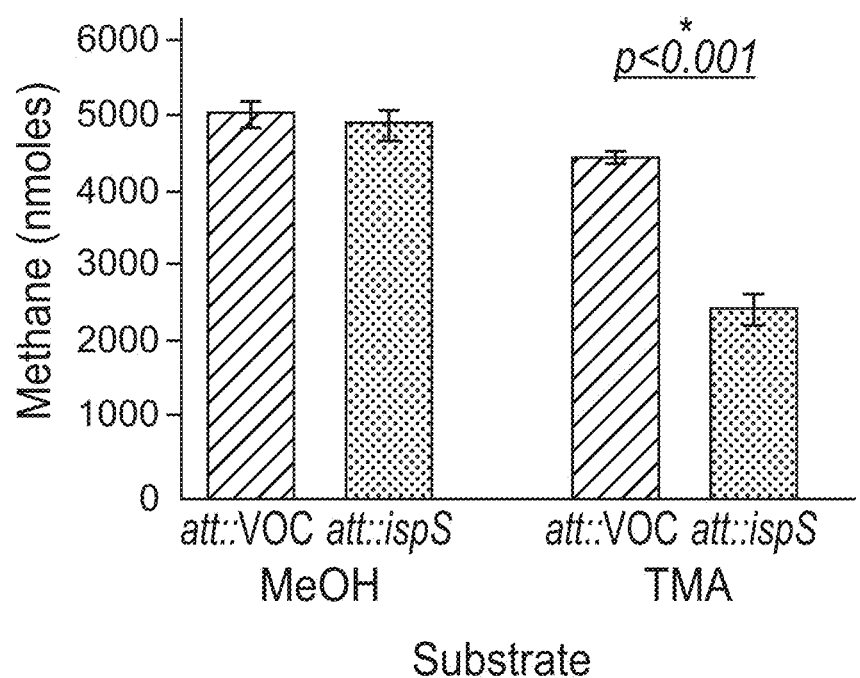
FIG. 5 depicts methane production by *M. acetivorans* grown on MeOH or TMA as analyzed in Example 1.

Endpoint methane production of the M. acetivorans vector only control (VOC), the parental plasmid, and ispS expressing strains of M. acetivorans, with and without CLS, grown anaerobically in 10 mL HS media containing 40 mM TMA was also analyzed. Methane production was measured by sampling headspace gasses using an Agilent Technologies 7890A Gas Chromatography system equipped with a flame ionization detector (FID). As shown in FIG. 5, methane production was decreased in both the ispS expressing strains as carbon should have been directed towards isoprene.

Figure 4:
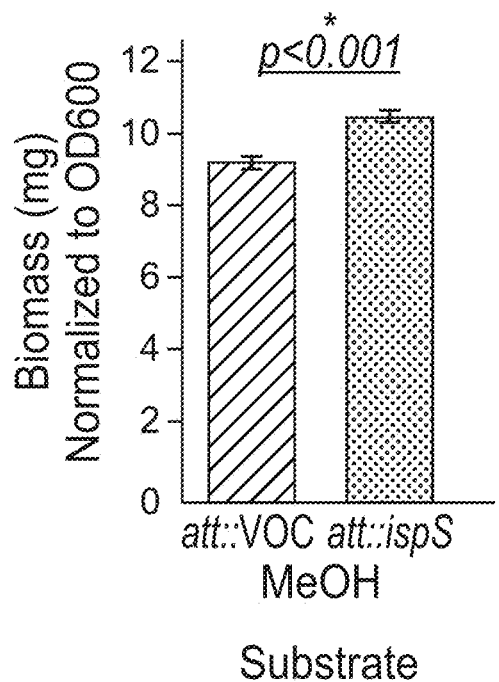
FIG. 4 depicts biomass produced by *M. acetivorans* growth on MeOH as analyzed in Example 1.

Experimental data shows ispS expressing cells grew better than vector only control (VOC) strains. As shown in FIG. 4, dry weight biomass measurements of cultures show ispS expressing cells accumulated more biomass than VOC cultures.

Endpoint methane production of the M. acetivorans vector only control (VOC) and an ispS expressing strain of M. acetivorans without CLS grown anaerobically in 10 mL HS media containing 125 mM methanol was also analyzed. Methane production was measured by sampling headspace gasses using an Agilent Technologies 7890A Gas Chromatography system equipped with a flame ionization detector (FID). As shown in FIG. 5, methane production was decreased in the ispS expressing strain as, again, carbon should have been directed towards isoprene.

A summary of the data shown in FIGS. 2-5 are shown in Table 1 below.

TABLE 1

Summarized data from FIGS. 2-5 containing respective standard deviations and p-values

| Strain | Growth Rate (hr) | Growth Rate std dev | Growth Rate p vs VOC | Methane production (nmol) | Methane std dev | % Methane yield |
|---|---|---|---|---|---|---|
| Methanosarcina acetivorans grown on 125 mM MeOH | | | | | | |
| att::VOC | 9.57 | 0.36 | 1 | 4948.06 | 146.01 | 100 |
| att::ispS - CLS | 9.01 | 0.42 | 0.77 | 4759.15 | 238.39 | 96.2 |
| Methanosarcina acetivorans grown on 40 mM trimethylamine | | | | | | |
| att::VOC | 11.75 | 0.31 | 1 | 20512.20 | 654.69 | 100 |
| att::ispS - CLS | 12.94 | 1.92 | 0.472 | 2926.99 | 359.00 | 14.3 |

Figure 6:
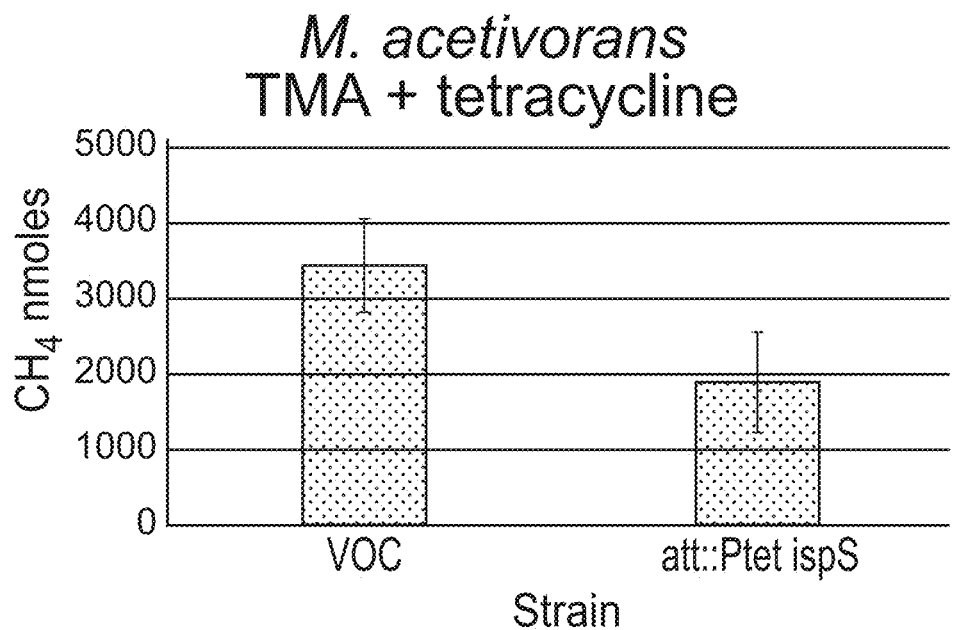
FIG. 6 depicts *M. acetivorans* methane production on TMA with tetracycline as analyzed in Example 1.

Similarly, endpoint methane production of a M. acetivorans vector only control (VOC) and an ispS expressing strain of M. acetivorans grown anaerobically in 10 mL HS media containing 100 mg/L tetracycline was analyzed. As shown in FIG. 6, methane production decreased in the ispS expressing strain.

Figure 7:
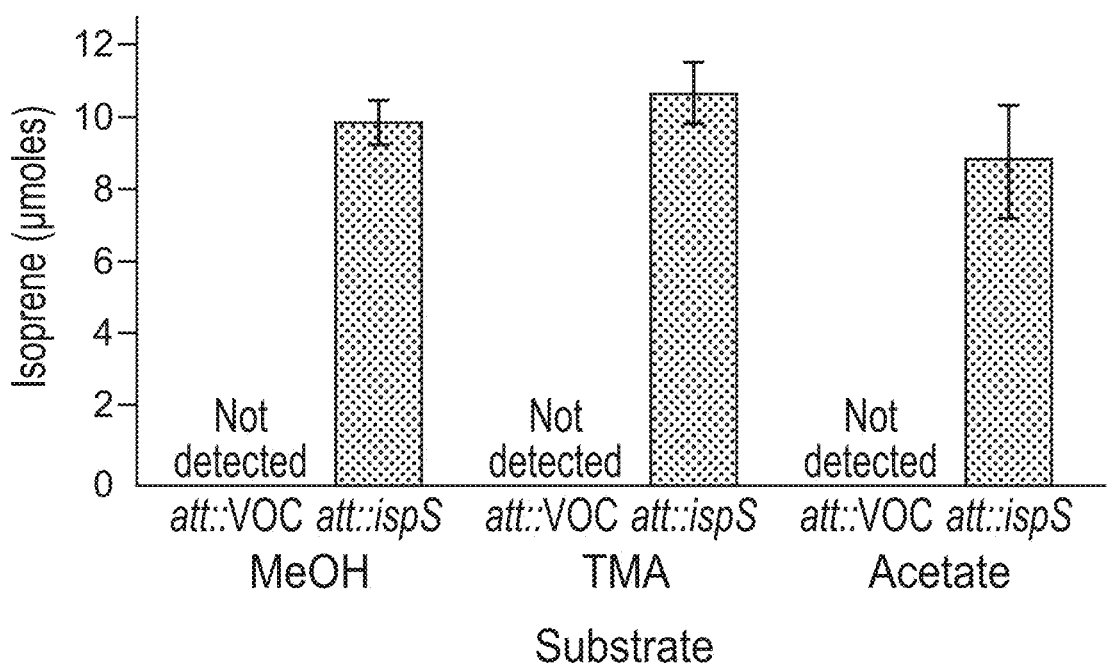
FIG. 7 depicts isoprene production by *M. acetivorans* grown on MeOH, TMA, or acetate as analyzed in Example 1.

Further, endpoint isoprene production of a M. acetivorans vector only control (VOC) and an ispS expressing strain of M. acetivorans grown anaerobically in 10 mL HS media containing either 125 mM methanol (MeOH), 40 mM trimethylamine (TMA), or 120 mM acetate were analyzed. As shown in FIG. 7, isoprene production increased in the ispS expressing strain on all tested substrates.

Figure 8:
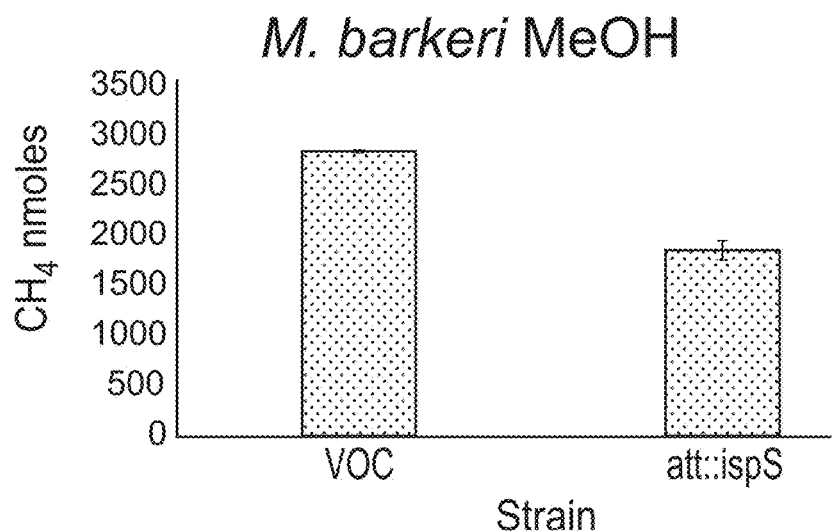
FIG. 8 depicts methane production by *M. barkeri* grown on MeOH as analyzed in Example 1.

Endpoint methane production of the M. barkeri vector only control (VOC), the parental plasmid, and ispS expressing strains of M. barkeri, with and without CLS, grown anaerobically in 10 mL HS media containing 40 mM TMA was also analyzed. Methane production was measured by sampling headspace gasses using an Agilent Technologies 7890A Gas Chromatography system equipped with a flame ionization detector (FID). As shown in FIG. 8, methane production was decreased in both the ispS expressing strains as carbon should have been directed towards isoprene.

Figure 9:
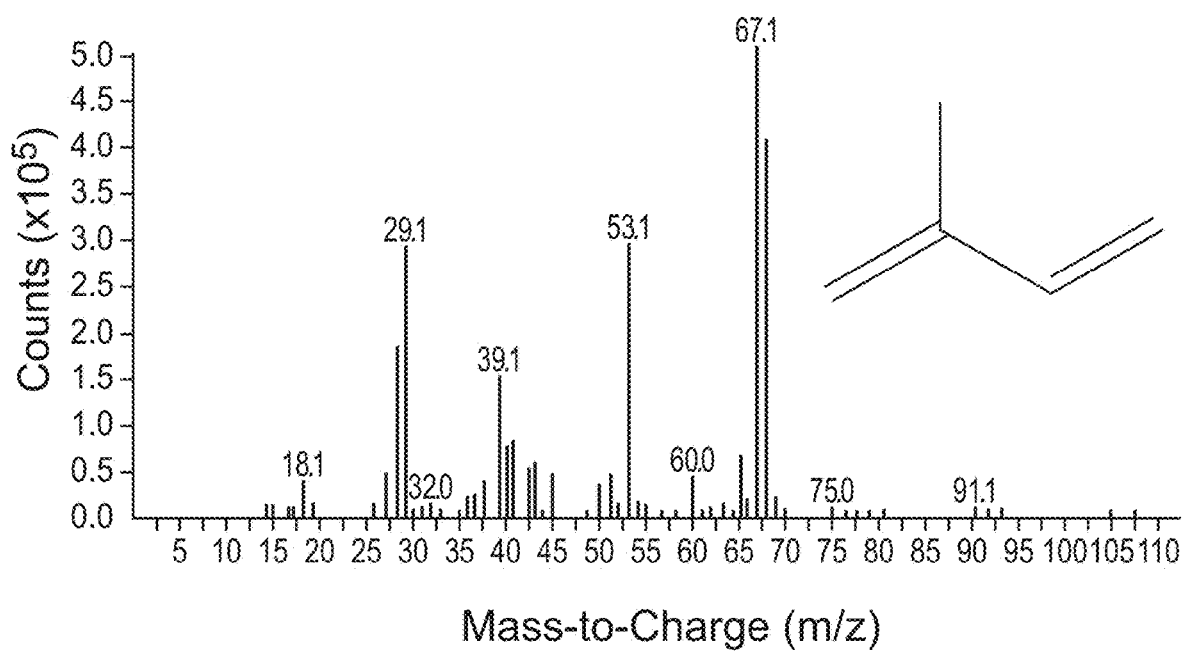
FIG. 9 depicts double-blind confirmation of isoprene production by *M. acetivorans* grown on MeOH as analyzed in Example 1.

FIG. 9 shows isoprene detected by gas chromatography and flame ionization detection using authentic isoprene standards (as in FIG. 7) is confirmed by gas chromatography mass spectrometry. Cells either expressing ispS or vector only control (VOC) were grown on 125 mM methanol. Samples from the cultures were collected and marked by number code. Data shown in FIG. 9 was collected by double-blinded sample submission to the University of Nebraska Biotechnology Core Facility. The mass to charge ratio of the dominant chemical species in the ispS expressing culture samples has a molecular mass of 67.1, which is consistent with a negative ion of isoprene ($C_5H_7$).

Figure 10:
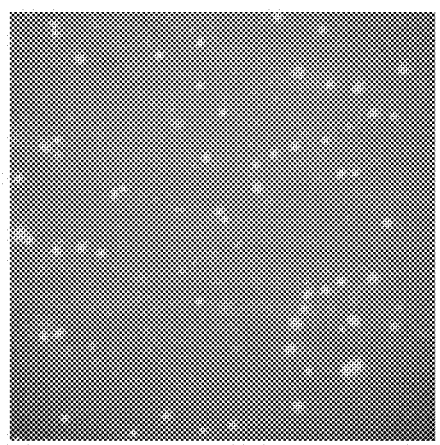
FIG. 10 depicts growth of *M. acetivorans* in synthetic wastewater as analyzed in Example 1.

It was determined that ispS expressing cells grow in synthetic wastewater, which has chemical and ionic composition very similar to authentic wastewater but with known components. The synthetic wastewater is composed of peptone (28 mg/L), meat extract (100 mg/L), urea (100 mg/L), $K_2HPO_4$ (28 mg), sodium chloride (7 mg/L), calcium chloride dehydrate (4 mg/L), magnesium sulfate septahydrate (2 mg/L), sodium bicarbonate (3.8 g/L), agarose (2.3 g/L), evaporated milk (30 mL), 125 mM methanol. As shown in FIG. 10, ispS expressing cells (blue) are capable of growing to high cell density in synthetic wastewater.

Figure 11A:
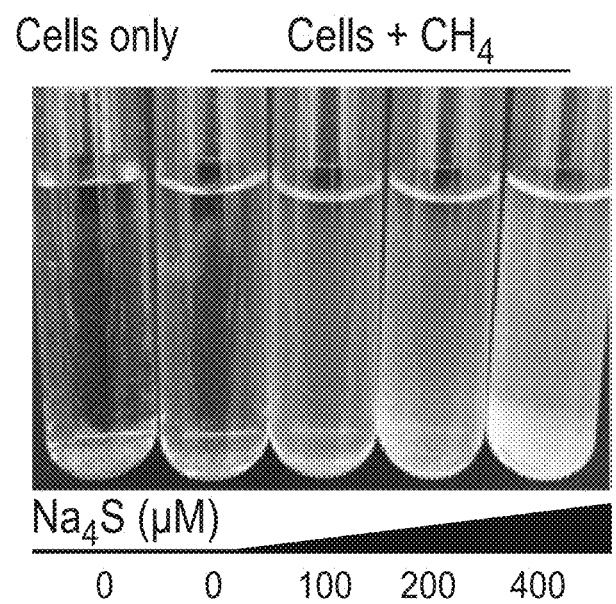
FIG. 11A depicts *M. acetivorans* growth on methane supplemented with sodium sulfide as analyzed in Example 1.
Figure 11B:
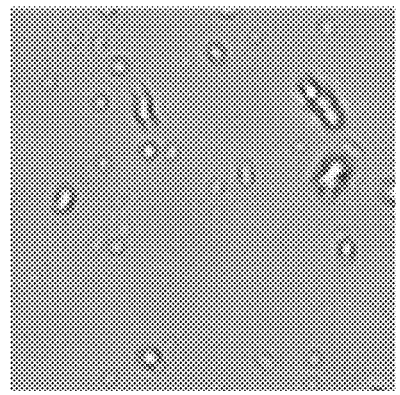
FIG. 11B depicts microscopy confirming growth of *M. acetivorans* on methane.
Figure 12A:
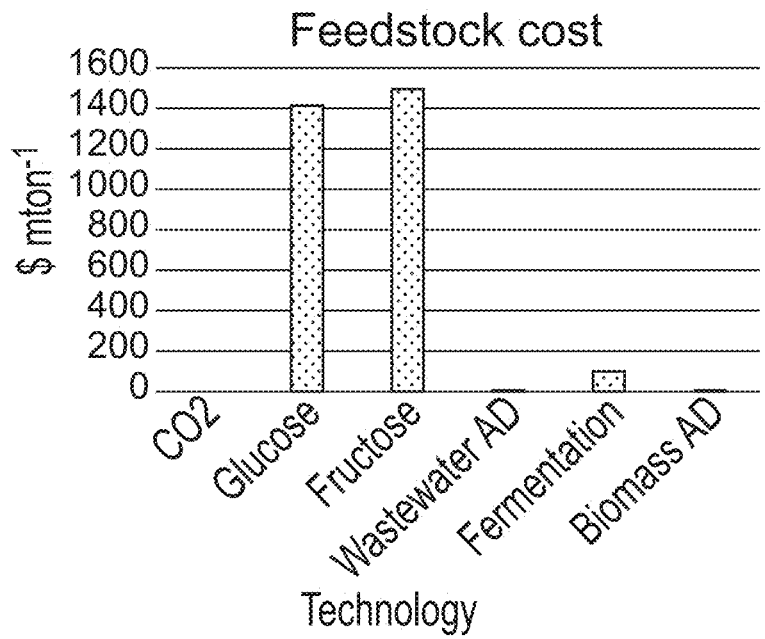
FIGS. 12A-12D depict the technoeconomic analysis of using methanogens to produce bioisoprene and other renewable products.
Figure 12B:
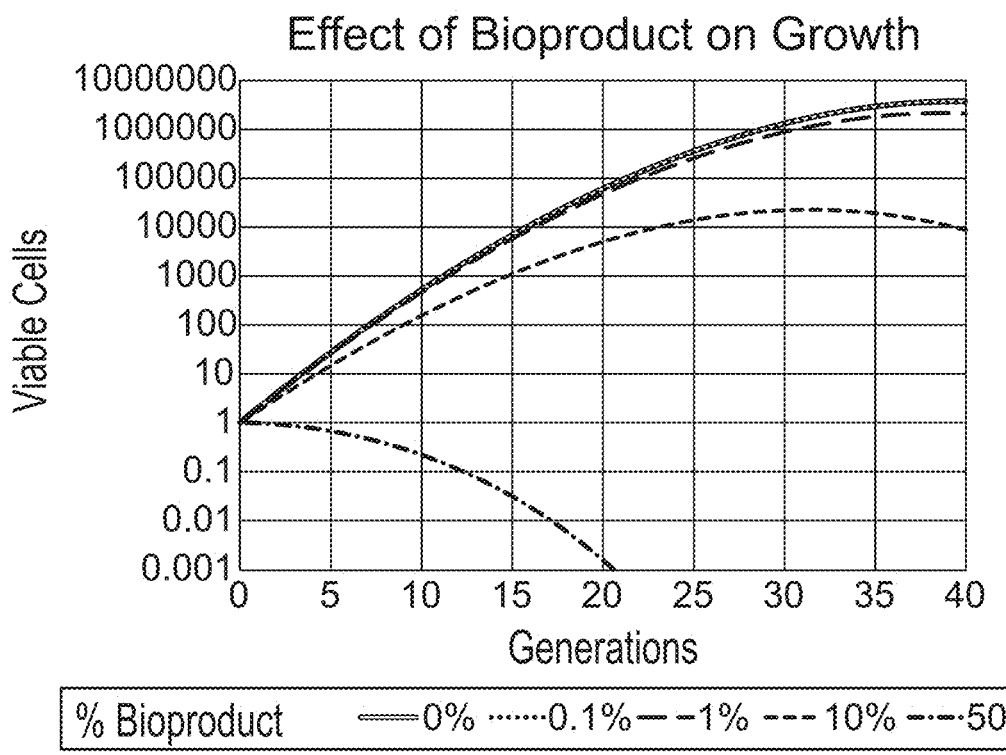
Figure 12C:
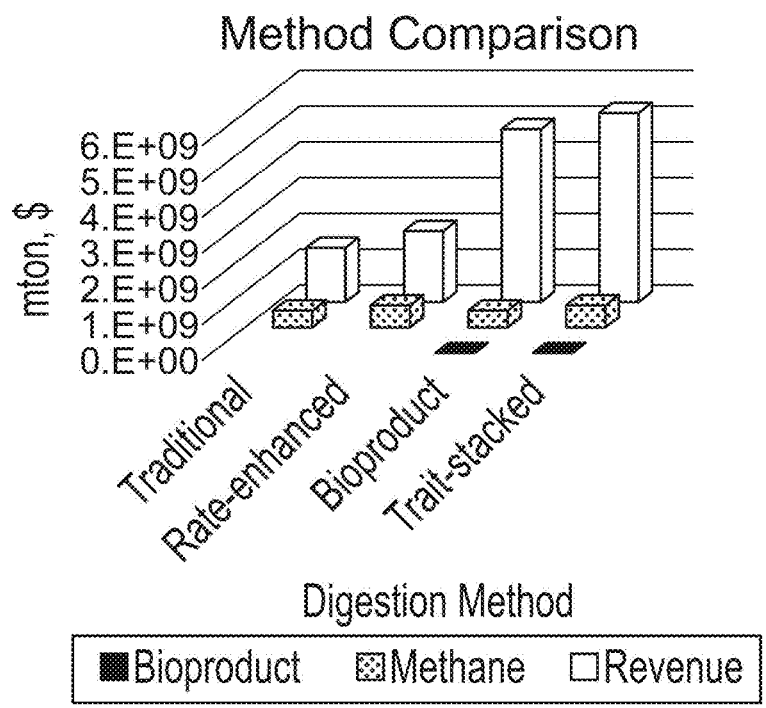
Figure 12D:
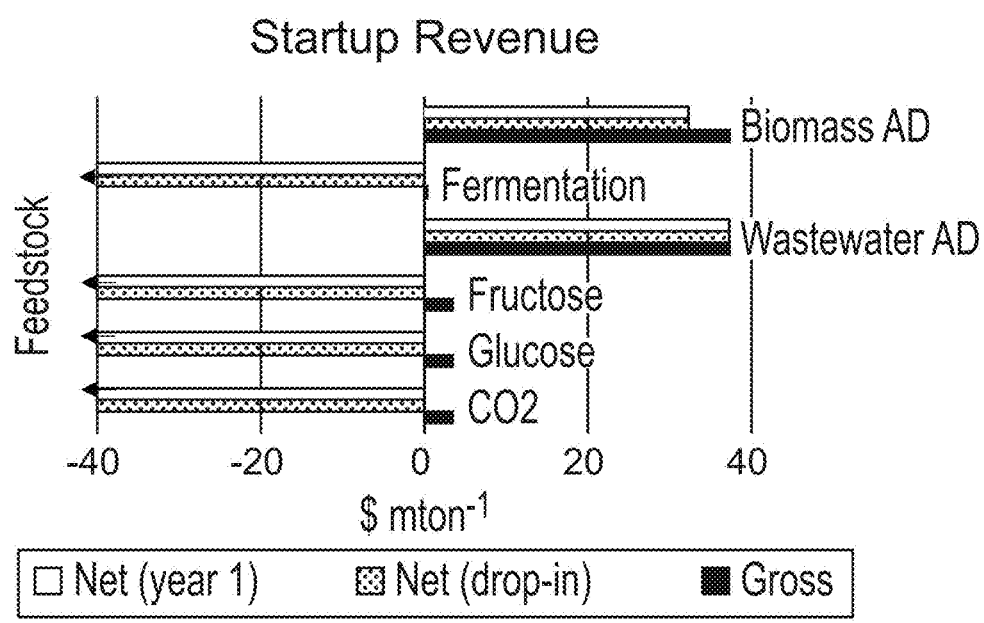

Recent published literature suggests *M. acetivorans* must be engineered to express a methyl-coenzyme M reductase enzyme from anaerobic methanotrophs to grow on methane as a carbon source (Soo V. W. et al. 2016. PMID: 26767617). The ability for the parent strain to grow on methane was also determined to evaluate if ispS expressing strains might also be able to grow on methane. *M. acetivorans* was added to high-salt (HS) culture medium that did not contain a carbon source. Pure methane was added to the culture headspace at 15 psi and cultures were incubated at 35° C. FIG. 11A shows that growth was enhanced by adding sodium sulfide ($Na_2S$). FIG. 11B shows that cultures contained viable growing cells (irregular spheres) at high cell density in addition to struvite crystals (rhombic shapes).

Table 2 below summarizes the yields of isoprene produced by *M. acetivorans* and *M. barkeri* on various substrates in batch cultures.

TABLE 2

Isoprene production of *Methanosarcina barkeri* and *Methanosarcina acetivorans* grown on various carbon sources

| Growth Substrate | Isoprene per 1 L culture (mg) |
|---|---|
| *Methanosarcina barkeri* | |
| $H_2:CO_2$[a] | 23.64 |
| 125 mM Methanol[a] | 2.45 |
| *Methanosarcina acetivorans* | |
| Methane[a] | 5.23 |
| 120 mM Acetate[b] | 62.42 ± 18.45 |
| 50 mM Trimethylamine[b] | 69.48 ± 16.89 |
| 125 mM Methanol[b] | 65.01 ± 16.08 |
| 120 mM Acetate:125 mM Methanol[a] | 25.89 |

[a]single culture measurement.
[b]average of three biological replicates

What is claimed is:

1. A transformed host cell comprising a vector comprising a nucleic acid encoding isoprene synthase having one of SEQ ID NO:1 and SEQ ID NO:2.

2. The transformed host cell of claim 1 wherein the cell is a microorganism selected from the group consisting of methanogen, methanotroph, and acetogen.

3. The transformed host cell of claim 2 wherein the cell is a *Methanosarcinales* strain.

4. The transformed host cell of claim 3 wherein the cell is selected from the group consisting of *Methanosarcinales acetivorans* and *Methanosarcinales barkeri*.

5. A vector comprising one of a nucleic acid of SEQ ID NO:1 and SEQ ID NO:2 encoding isoprene synthase.

6. A method of preparing a transformed microbial strain capable of producing isoprene, the method comprising:
    preparing a vector comprising a nucleic acid encoding a *Populus alba* isoprene synthase, wherein the nucleic acid is one of SEQ ID NO:1 and SEQ ID NO:2 by preparing a primer comprising a nucleotide sequence selected from the group consisting of SEQ ID NO:3, SEQ ID NO:4 and SEQ ID NO:5; amplifying a template *Populus alba* isoprene synthase cDNA with the primer to obtain an isoprene synthase cDNA; annealing the isoprene synthase cDNA with a plasmid to obtain the vector;
    introducing the vector into a host cell from a microorganism selected from the group consisting of methanogen, methanotroph and acetogen; and
    anaerobically culturing the transformed host cell including the vector in a culture medium comprising a carbon source.

7. The method of claim 6 wherein the host cell is a cell selected from the group consisting of *Methanosarcinales acetivorans* and *Methanosarcinales barkeri*.

8. The method of claim 6 wherein culturing the transformed host cell including the vector comprises culturing the transformed host cell anaerobically in high salt medium at 35° C. until $OD_{600}$ reaches between about 0.5 and about 0.7.

9. The method of claim 6 wherein the carbon source is selected from the group consisting of carbon dioxide, methanol, methylamines, methylsulfides, methylated metal/metalloids, formate, carbonate, graphite, carbon monoxide, acetate, methane, and combinations thereof.

* * * * *